(12) United States Patent
Rubio

(10) Patent No.: US 8,105,302 B2
(45) Date of Patent: Jan. 31, 2012

(54) ADJUSTABLE WIDTH AND LENGTH SANITARY NAPKIN AND PANTY LINER

(75) Inventor: Ilse Rubio, Los Angeles, CA (US)

(73) Assignee: Isle Rubio

( * ) Notice: Subject to any disclaimer, the term of this patent is extended or adjusted under 35 U.S.C. 154(b) by 0 days.

(21) Appl. No.: 11/811,497

(22) Filed: Jun. 11, 2007

(65) Prior Publication Data

US 2008/0009818 A1    Jan. 10, 2008

Related U.S. Application Data

(60) Provisional application No. 60/813,832, filed on Jun. 14, 2006.

(51) Int. Cl.
*A61F 13/15* (2006.01)
*A61F 13/20* (2006.01)

(52) U.S. Cl. ......... 604/385.11; 604/385.01; 604/385.16; 604/385.14; 604/387

(58) Field of Classification Search ............. 604/385.01, 604/385.11–385.16, 385.201
See application file for complete search history.

(56) References Cited

U.S. PATENT DOCUMENTS 5,704,929 A * 1/1998 Bien ........................ 604/385.23

* cited by examiner

*Primary Examiner* — Michele M Kidwell

(57) ABSTRACT

A single adjustable sanitary napkin or panty liner includes both folding panels and tear-away panels to adjust the width and/or the length to a particular woman or outfit. The panels may be folded and/or torn away to adjust the shape and the size of the sanitary napkin or panty liner. Adhesive strips may be provided to retain folded panels. Thus a single sanitary napkin or panty liner fits the needs of a variety of women and outfits.

19 Claims, 8 Drawing Sheets

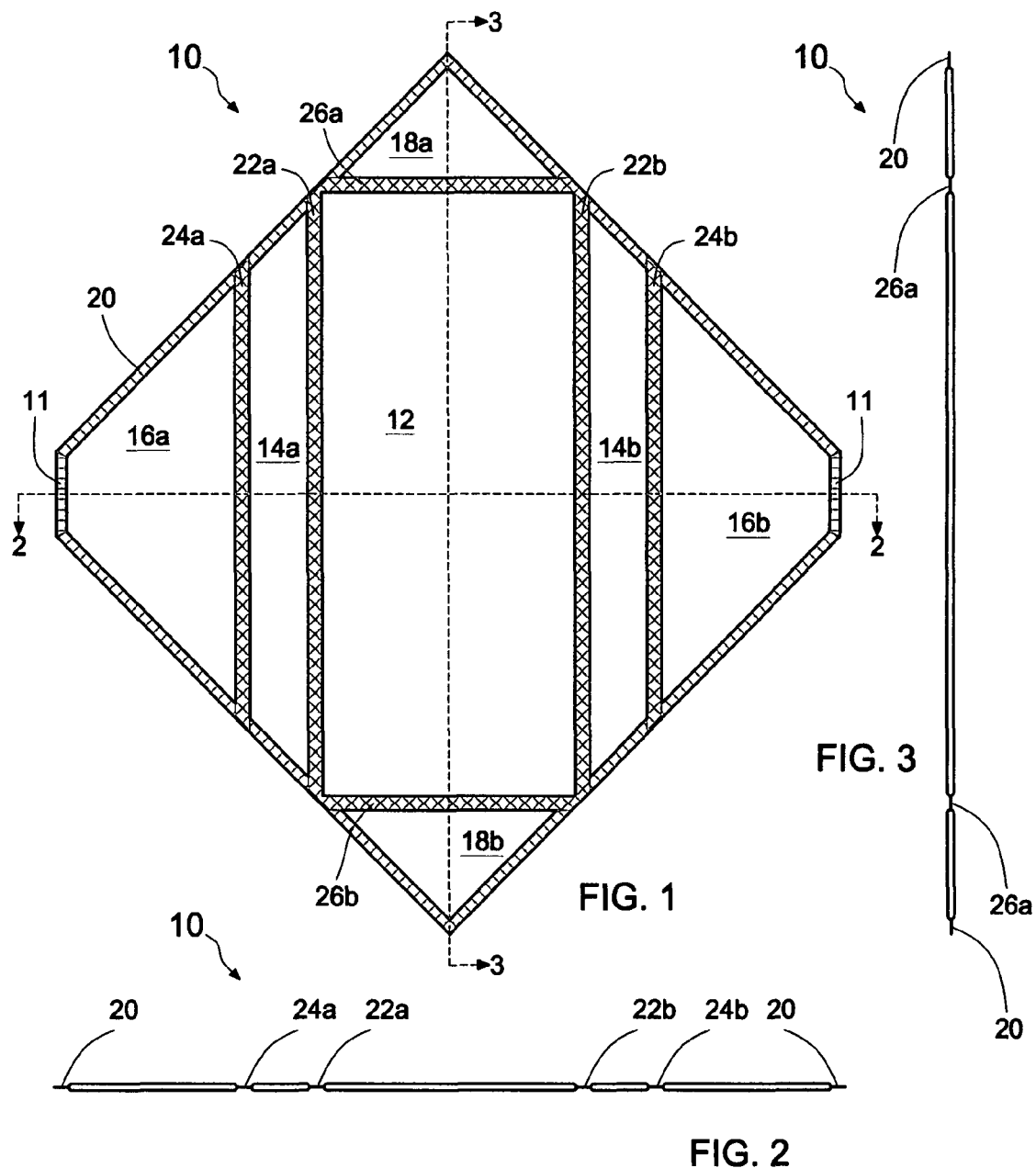

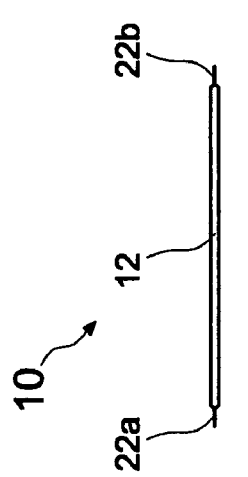
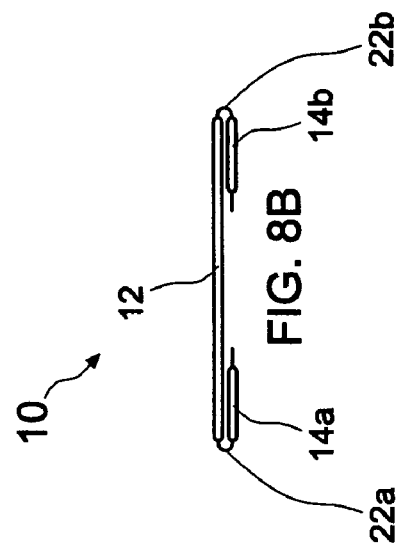
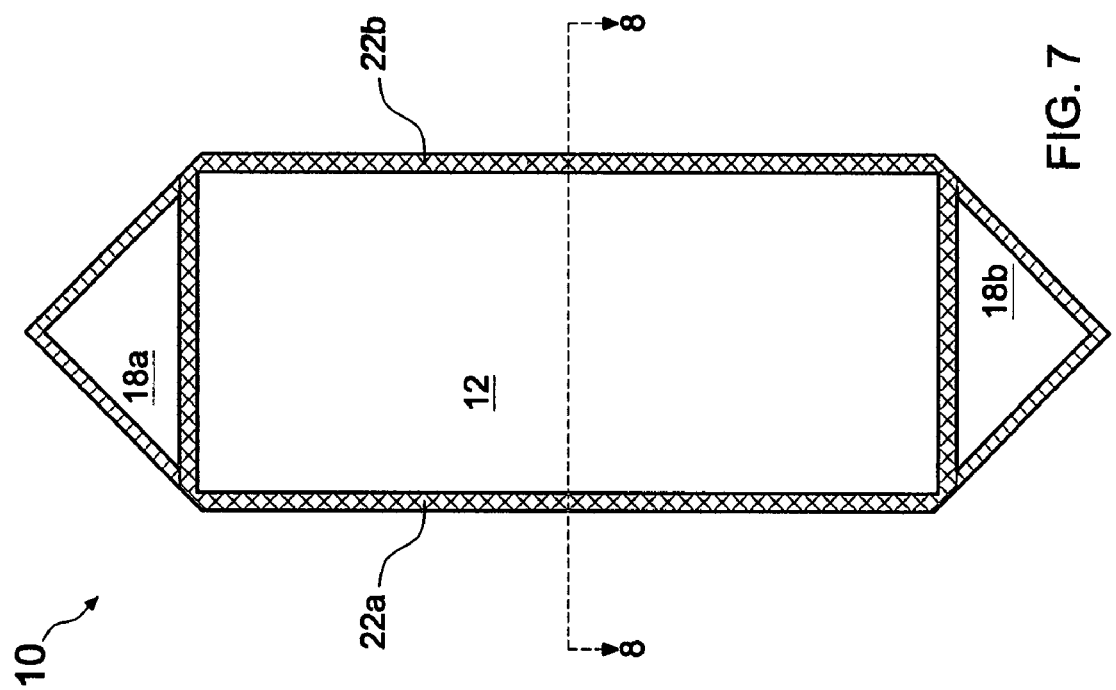

ADJUSTABLE WIDTH AND LENGTH SANITARY NAPKIN AND PANTY LINER

CROSS REFERENCES TO RELATED APPLICATIONS

This application claims priority to Provisional application No. 60/813,832 filed on Jun. 14, 2006

BACKGROUND OF THE INVENTION

The present invention relates to women's hygiene and in particular to a sanitary napkin and/or to a panty liner which may be adjusted in width and/or length.

Women may have different anatomical proportions and wear various clothing which fits differently. As a result, no single sanitary napkin or panty liner is a good fit to all women, or a good fit to a woman wearing a variety of clothing. Some sanitary napkins and/or panty liners may be adjusted in length and some may be adjusted in width, but known sanitary napkins and panty liners fail to allow adjustment in both length and width. As a result, it is often difficult to obtain a good fit.

BRIEF SUMMARY OF THE INVENTION

The present invention addresses the above and other needs by providing a single adjustable sanitary napkin or panty liner includes both folding panels and tear-away panels to adjust the width and/or the length to a particular woman or outfit. The panels may be folded and/or torn away to adjust the shape and the size of the sanitary napkin or panty liner. Adhesive strips may be provided to retain folded panels. Thus a single sanitary napkin or panty liner fits the needs of a variety of women, sizes, proportions, or outfit.

BRIEF DESCRIPTION OF THE SEVERAL VIEWS OF THE DRAWING

The above and other aspects, features and advantages of the present invention will be more apparent from the following more particular description thereof, presented in conjunction with the following drawings wherein:

FIG. 1 is a top view of an adjustable sanitary napkin or panty liner according to the present invention.

FIG. 2 is a cross-sectional view of the adjustable sanitary napkin or panty liner taken along line 2-2 of FIG. 1

FIG. 3 is a cross-sectional view of the adjustable sanitary napkin or panty liner taken along line 3-3 of FIG. 1

FIG. 7 shows the adjustable sanitary napkin or panty liner with inside panels folded or torn away.

FIG. 8A is a cross-sectional view of the adjustable sanitary napkin or panty liner with inside panels torn away, taken along line 8-8 of FIG. 7.

FIG. 8B is a cross-sectional view of the adjustable sanitary napkin or panty liner with inside panels folded, taken along line 8-8 of FIG. 7.

DETAILED DESCRIPTION OF THE INVENTION

Figure 4:
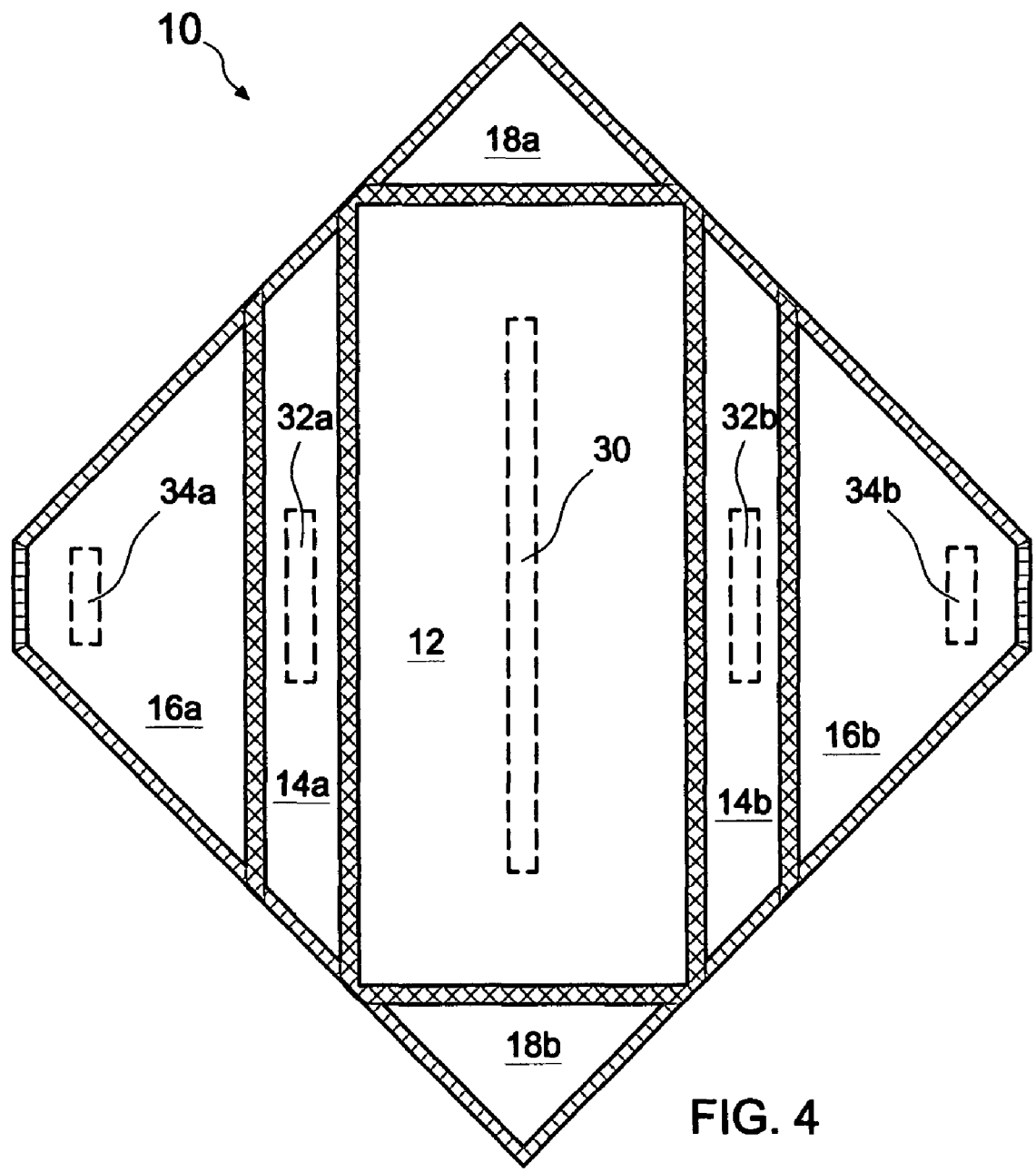
FIG. 4 shows adhesive strips attached panels of the adjustable sanitary napkin or panty liner.

The following description is of the best mode presently contemplated for carrying out the invention. This description is not to be taken in a limiting sense, but is made merely for the purpose of describing one or more preferred embodiments of the invention. The scope of the invention should be determined with reference to the claims.

An adjustable sanitary napkin, panty liner, or incontinence pad 10 (or hygienic pad) according to the present-invention is shown in FIG. 1, a cross-sectional view of the adjustable sanitary napkin, panty liner, or incontinence pad. 10 taken along line 2-2 of FIG. 1 is shown in FIG. 2, and a cross-sectional view of the adjustable sanitary napkin, panty liner, or incontinence pad 10 taken along line 3-3 of FIG. 1 is shown in FIG. 3. The adjustable napkin, liner, or pad 10 comprises a diamond shape with truncated or flattened outside points to form flats 11. The adjustable sanitary napkin, panty liner, or incontinence pad 10 includes several absorbent panels. The panels comprise a center rectangular panel 12, a left inside panel 14a, a right inside panel 14b, a left outside panel 16a, a right outside panel 16b, a top panel 18a, and a bottom panel 18b. While the top and bottom panels 18a and 18b are shown pointed, i.e. triangles tapering from a wider base attached to the center panel to a narrow end or point, they may also include truncated ends or flats 11 shown on outside panels 16a and 16b. Likewise, the inside panels 14a, 14b taper from a wider base attached to center panel 12 along seams 22a, 22b to narrower edge along seam 24a, and outside panels taper from a wider base attached to seam 24a to narrower outside ends 11. A bonded pad edge 20 extends around the perimeter of the napkin, liner, or pad 10.

Seams are provided between the panels to facilitate folding or tearing to remove panels. A left inside seam 22a resides between the center panel 12 and the left inside panel 14a, and a right inside seam 22b resides between the center panel 12 and the right inside panel 14b. A left outside seam 24a resides between the left inside panel 14a and the left outside panel 16a, and a right outside seam 24b resides between the right inside panel 14b and the right outside panel 16b. Outside seams 24a,b are seen to be parallel to inside seams 24a,b. A top seam 26a resides between the top panel 18a and the center panel 12, and a bottom seam 26b resides between the bottom panel 14b and the center panel 12. In the illustrated embodiment seams 22a,b, 24a,b and 26a,b are straight line seams, and top seams 26a,b are shorter than inside seams 22a,b. The inside panels and outside panels may be seen as portions of generally triangular or trapezoidal side panels divided by the outside seams 24a and 24b into the aforesaid inside panels and outside panels. The panels 14a, 14b, 16a, 16b, 18a, and 18b may be folded or torn away along the seams to adjust the shape of the adjustable sanitary napkin or panty liner as shown subsequent figures. The panels 14a, 14b, 16a, 16b, 18a, and 18b may be made from known absorbent material used for sanitary napkin, panty liner or incontinence pad, or may be any other suitable material. In the embodiment shown in the drawings the seams have a seam thickness smaller than the seam width between the panels on either side of the seam, and the seam thickness is substantially smaller than the thickness of the absorbent material in the various panels of the pad.

The folding and tear away panels 14a, 14b, 16a, 16b, 18a, and 18b thus provide an adjustable sanitary napkin, panty liner or incontinence pad. The resulting napkin, liner, or pad 10 is multifunctional, because it adjusts in both length and width into different geometrical shapes, providing a single pad for a variety of uses. The napkin, liner, or pad 10 is comprised of a diamond shape with flattened outside points to form flats and has a rectangular center area with straight or curve seams. The napkin, liner, or pad 10 may be folded in different ways to adjust in length and width into seven or more shapes, from rectangular, to full diamond (or square using the four corners), half diamond or circle. The combined width of the panel 16a added to the panel. 14a, or the panel 16b added to the panel 14b, is preferably less than the width of the rectangular area 12, there by facilitating folding the panels under the center rectangle. The inside panels 14a and 14b when folded, should preferably be narrower than half the width of the rectangular area 12. Top and bottom panels 18a and 18b, when folded, should be at least ¼ to ½ the length of the rectangular area 12. The napkin, liner, or pad 10 total length is approximately the addition of the rectangular area 12 length and the length of the top and the bottom panels 18a and 18b. The center rectangular panel 12 has a width of at least approximately 1.5 inches to 2.0 inches and a length of at least approximately 4 inches.

Adhesive strips may be attached to the panels of the adjustable napkin, liner, or pad 10 as shown in FIG. 4 to facilitate retaining folded panels. An adhesive strip 30 may be attached to the panel 12, an adhesive strip 32a may be attached to the panel 14a, an adhesive strip 32b may be attached to the panel 14b, an adhesive strip 34a may be attached to the panel 16a, and an adhesive strip 34b may be attached to the panel 16b. The adhesive strips may be adhered to either the napkin, liner, or pad 10 or to clothing (for example, panties) worn by the user. All the adhesive strips 34a, 34b, 32a, 32b, and 30 may be wider, thinner or a combination there of, and strip 30 may also be wider enough to have adhesive on the entire panel 12.

Figure 4A:
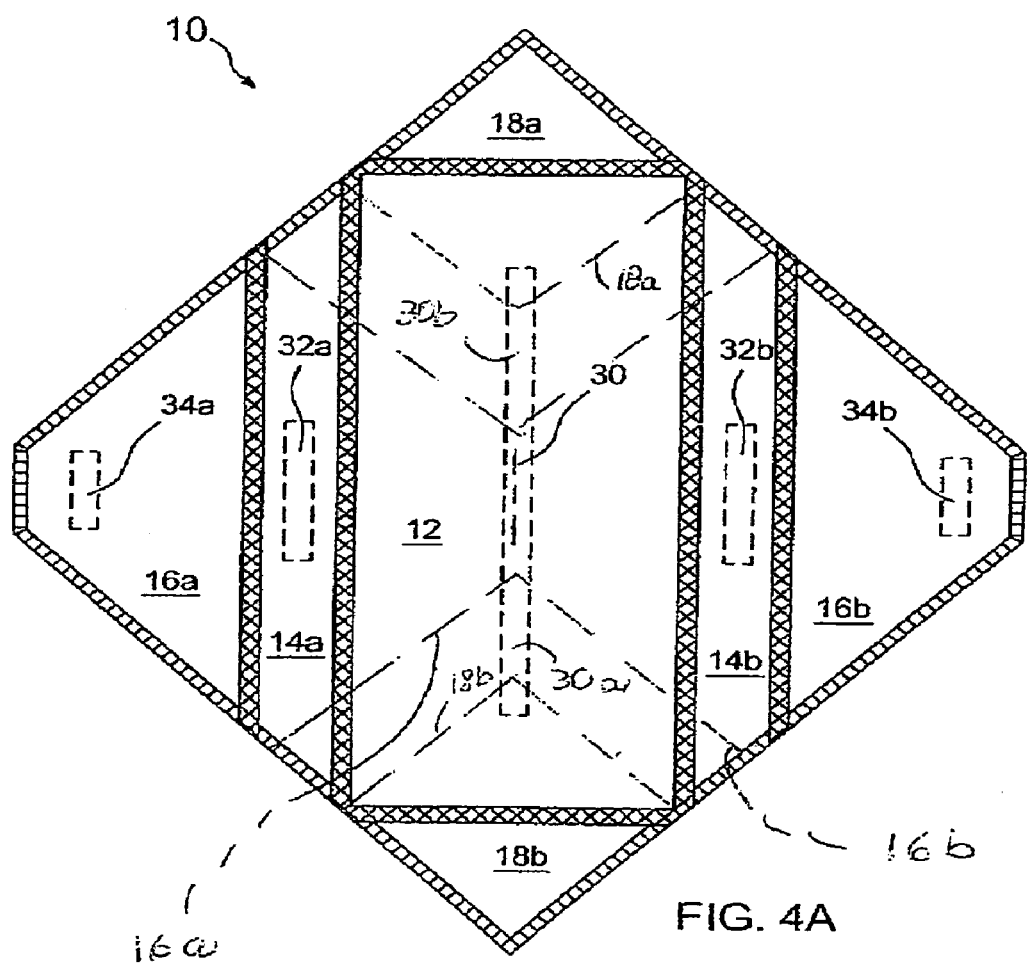
Figure 4C:
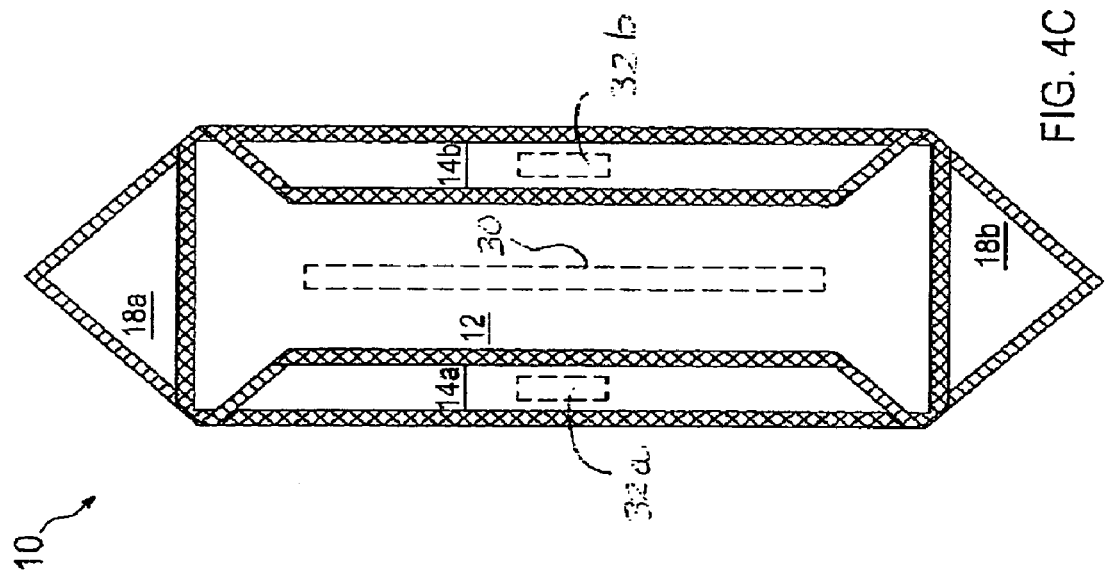
Figure 4B:
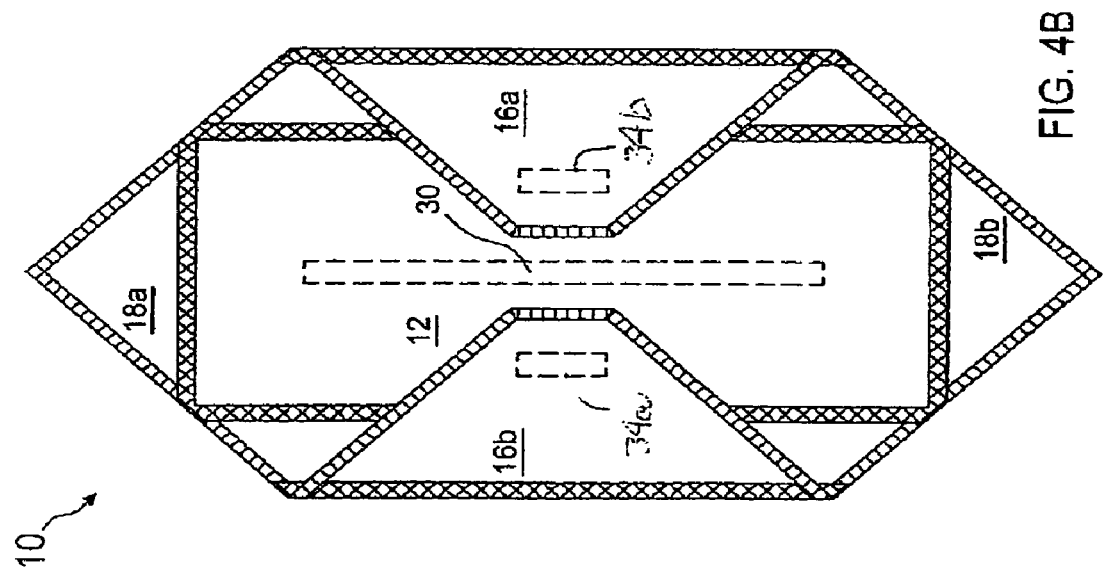

From FIG. 4 it is evident that when end panels 16a, 16b are folded inwardly towards center strip 30 along their respective fold lines 24a, 24b in FIG. 1, the resulting positions of the end panels are as indicated in FIG. 4A where phantom lined panels 16a, 16b are shown folded inwardly over side panels 14a, 14b respectively and onto center panel 12. The truncated ends of panel 16a, 16b lie on center strip 30, but leave substantial portions of the strip exposed on either side of the folded panels, with only a relatively small center portion of the strip 30 being covered by folded panels 16a, 16b. On FIGS. 4B and 4C, the truncated ends of panel 16a, 16b, 14a, 14b lie near the center strip 30.

Top and bottom panels 18a, 18b are similarly shown folded inwardly along their respective fold lines 26a, 26b in FIG. 1. In the phantom lined folded condition of FIG. 4A it is seen that the three pointed tips of the top and bottom panels lie on respective ends of the center strip 30, but leave a large mid portion of strip 30 exposed and uncovered by the end panels.

Consequently, with either the top and bottom panels 18a, 18b folded inwardly onto center panel 12, or end panels 16a, 16b inwardly folded onto center panel 12 substantial portions of the adhesive center strip 30 remain exposed and available for fastening the pad 10 to a garment.

Figure 6A:
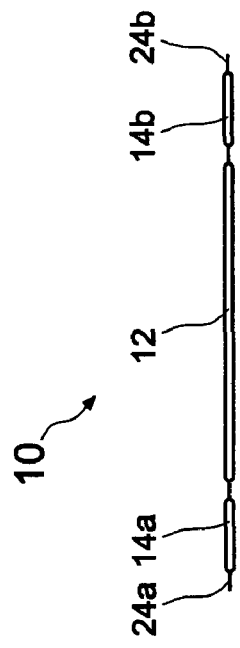
FIG. 6A is a cross-sectional view of the adjustable sanitary napkin or panty liner with outside panels torn away, taken along line 6-6 of FIG. 5.
Figure 6B:
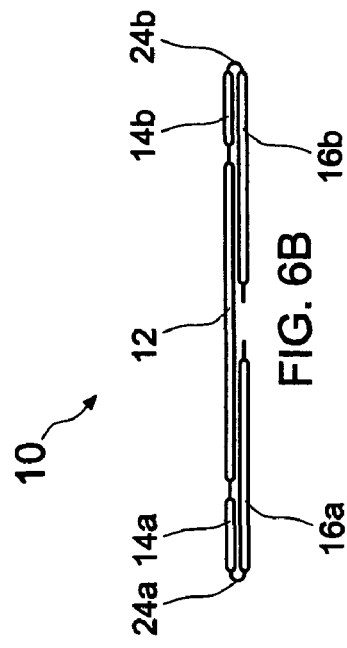
FIG. 6B is a cross-sectional view of the adjustable sanitary napkin or panty liner with outside panels folded, taken along line 6-6 of FIG. 5.
Figure 5:
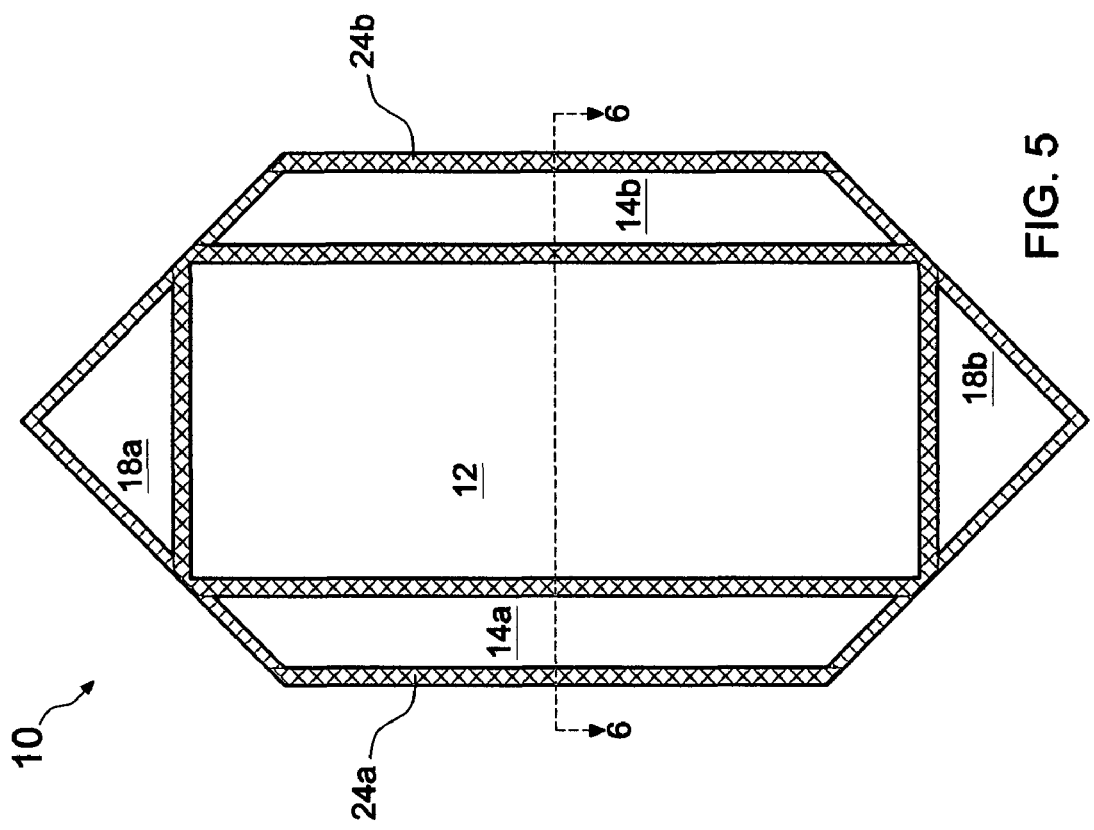
FIG. 5 shows the adjustable sanitary napkin or panty liner with outside panels folded or torn away.

The adjustable sanitary napkin or panty liner 10 with outside panels 16a and 16b folded or torn away is shown in FIG. 5, a cross-sectional view of the adjustable sanitary napkin or panty liner with outside panels 16a and 16b torn away, taken along line 6-6 of FIG. 5 is shown in FIG. 6A, and a cross-sectional view of the adjustable sanitary napkin or panty liner with outside panels folded, taken along line 6-6 of FIG. 5 is shown in FIG. 6B. The panels 14a and 14b provide wider coverage then the center 12 alone, allowing for the retention of more fluids. The overall length of the napkin, liner, or pad 10 is the addition of the length of center 12 and the length of the top and the bottom panels 18a and 18b.

The adjustable napkin, liner, or pad 10 is shown in FIG. 7 with inside panels 14a and 14b folded or torn away, providing a narrow napkin, liner, or pad 10. A cross-sectional view of the adjustable sanitary napkin or panty liner 10 with inside panels 14a and 14b torn away, taken along line 8-8 of FIG. 7 is shown in FIG. 8A, and a cross-sectional view of the adjustable sanitary napkin or panty liner 10 with inside panels 14a and 14b folded, taken along line 8-8 of FIG. 7 is shown in FIG. 8B. The panels 18a and 18b may be folded into clothing (for example, panties) also. The length of the panels 18a and 18b, when folded, should be at least ¼ to ½ longer than the length of the center 12.

Figure 12:
FIG. 12 is the adjustable sanitary napkin or panty liner with inside panels, outside panels, and the top panels folded or torn away.
Figure 11:
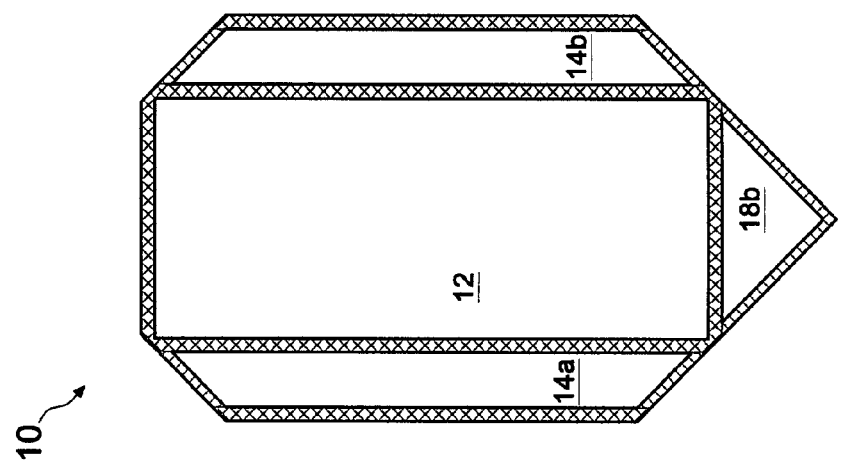
FIG. 11 is the adjustable sanitary napkin or panty liner with outside panels and the top panels folded or torn away.
Figure 10:
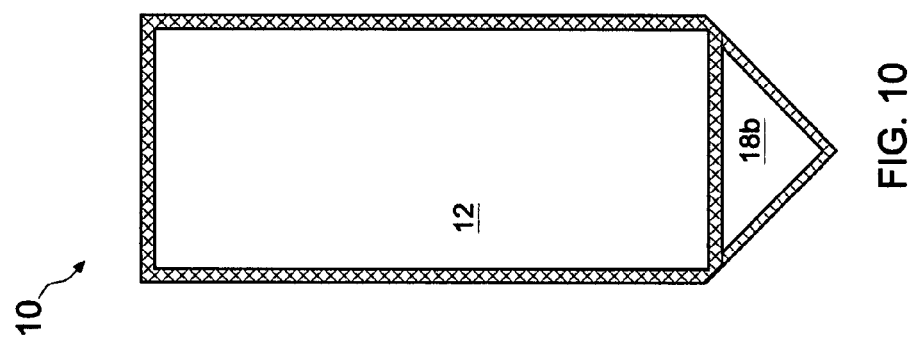
FIG. 10 is the adjustable sanitary napkin or panty liner with inside panels and the top panels folded or torn away.
Figure 9:
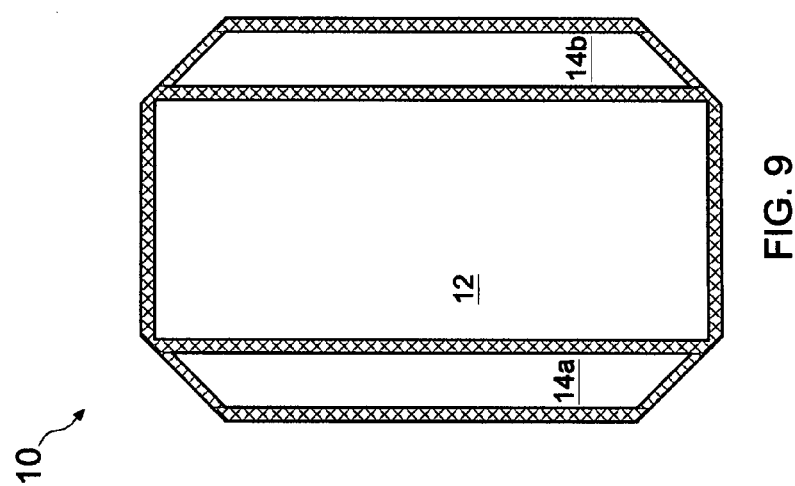
FIG. 9 is the adjustable sanitary napkin or panty liner with outside panels and top and bottom panels folded or torn away.

The adjustable sanitary napkin or panty liner 10 with outside panels 16a and 16b and top and bottom panels 18a and 18b folded or torn away, is shown in FIG. 9. The adjustable sanitary napkin or panty liner 10 with inside panels 14a and 14b and the top panel 18a folded or torn away is shown in FIG. 10. The adjustable sanitary napkin or panty liner 10 with outside panels 16a, and 16b and the top panel 18a folded for torn away is shown in FIG. 11. The adjustable sanitary napkin or panty liner 10 with the inside panels 14a and 14b, the outside panels 16a, and 16b and the top panel 18a folded for torn away is shown in FIG. 12. Thus, any combination of panels may be folded or torn away to adjust the size of the adjustable sanitary napkin or panty liner 10 for a particular woman or outfit. In each instance, by folding or tearing away specific panels, the adjustable sanitary napkin or panty liner 10 may be configured to fit a woman's anatomy or clothing, and provide the best coverage and absorption available.

Figure 13:
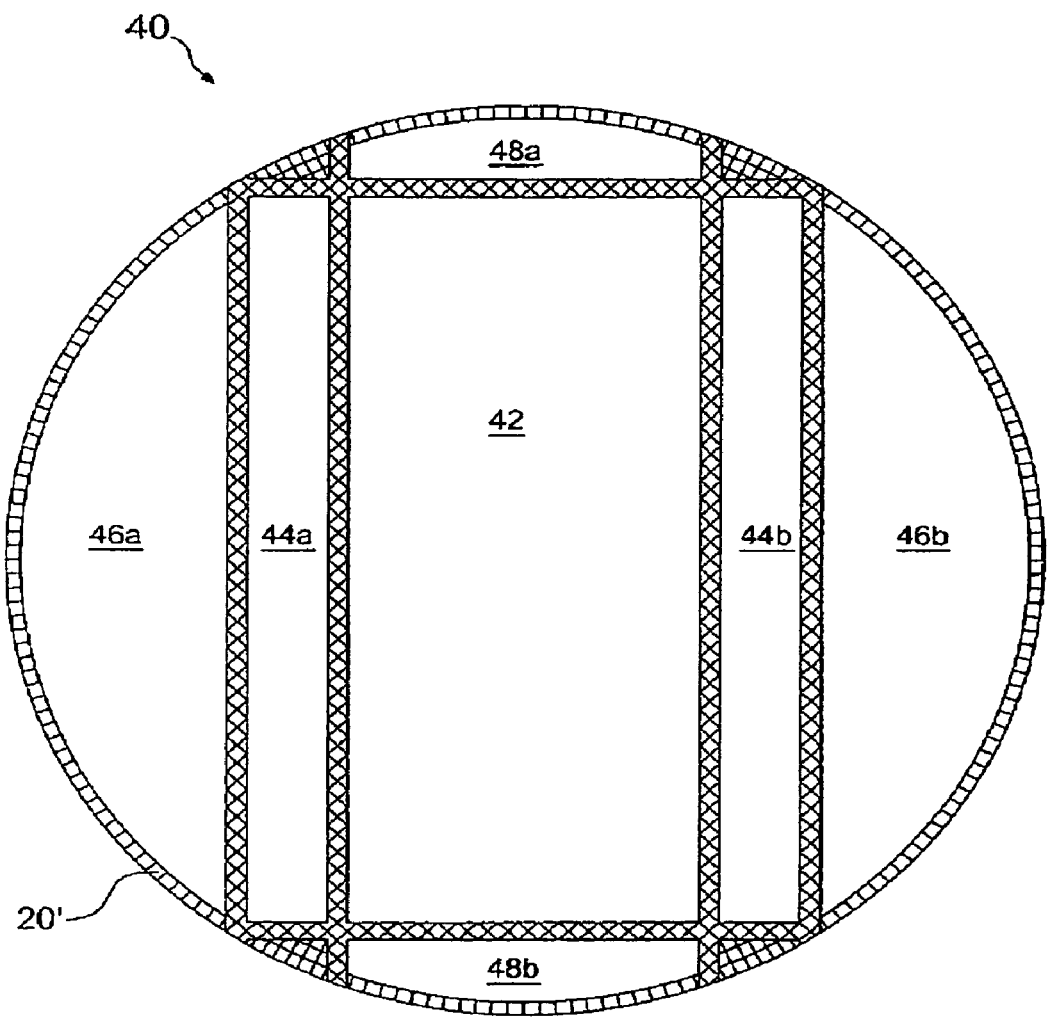
FIG. 13 is a round embodiment of the adjustable sanitary napkin or panty liner according to the present invention.

A round embodiment of the adjustable sanitary napkin or panty liner 40 according to the present invention is shown in FIG. 13, where a rectangular center panel 42 is circumscribed by a circular pad edge 20' instead of being circumscribed by the diamond shaped pad edge 20 as in FIGS. 1 and 4. The adjustable sanitary napkin or panty liner 40 may be adjusted as described above for the adjustable sanitary napkin or panty liner 10. The adjustable sanitary napkin or panty liner according to the present invention may further be wider or longer than the adjustable sanitary napkin or panty liner 10, and may be oval or elliptical. Any adjustable sanitary napkin or panty liner having panels joined by seams allowing folding for tearing is intended to come within the scope of the present invention, regardless changes of shape, or of absorbent material.

The sanitary napkin or panty liner 10 is used by folding or tearing away separately, the top or bottom panel 18a or 18b, and/or the outside panels 16a or 16b, and/or the inside panels 14a or 14b. The sanitary napkin or panty liner 10 is thus adjustable in length and width into different shapes and sizes. The panels 14a, 14b, 16a, 16b, 18a, and 18b may be torn or folded along seams.

While the invention herein disclosed has been described by means of specific embodiments and applications thereof, numerous modifications and variations could be made thereto by those skilled in the art without departing from the scope of the invention set forth in the claims.

I claim:

1. An adjustable sanitary napkin, panty liner or incontinence pad of generally diamond shape with four pad edges and four pad corners, a top side and a bottom side;

four substantially straight seams in said pad defining a rectangular center panel having four panel corners each touching a respective one of said four pad edges at a location intermediate said pad corners thereby defining two end panels and two side panels each attached to one of said four seams such that said end panels and said side panels each taper to narrower ends, said side panels being each divided by an outside seam parallel into a inside panel and an outside panel;

such that one or more of said side panels may be folded or torn along said seams thereby to alter the shape and size of said pad; and at least one adhesive strip on said bottom side for holding any of said end panels, said outside panels and said inside panels folded under said center panel for altering the shape and size of said pad.

2. The adjustable sanitary napkin, panty liner or incontinence pad of claim 1 wherein two of said end panels are attached to shorter seams and said side panels are attached to longer seams such that said end panels are smaller than said side panels.

3. The adjustable sanitary napkin, panty liner or incontinence pad of claim 2 wherein each of said end panels tapers to a pointed end and said side panels have truncated ends.

4. The adjustable sanitary napkin, panty liner or incontinence pad of claim 1 wherein said least one adhesive strip comprises a center adhesive strip on said bottom side of said center panel for holding either or both of said end panels in a folded condition under the center panel.

5. The adjustable sanitary napkin, panty liner or incontinence pad of claim 4 further comprising an adhesive strip on said bottom side of each said side panel for holding either or both of said side panels in a folded condition under the center panel.

6. The adjustable sanitary napkin, panty liner or incontinence pad of claim 4 wherein said outside panels have outside ends which lie near each other and against said center adhesive strip when said outside panels are folded under said center panel.

7. The adjustable sanitary napkin, panty liner or incontinence pad of claim 4 further comprising an adhesive strip on said bottom side of each said inside panel and outside panel for holding either said outside panels folded under said inside panels and said center panel, or said inside panels folded under said center panel after tearing away each of said outside panels along said outside seam.

8. The adjustable sanitary napkin, panty liner or incontinence pad of claim 7 wherein said adhesive strips on said outside panels lie intermediate said center adhesive strip and said adhesive strips on said inside panels when said outside panels are folded along said outside seam under said center panel, such that all said adhesive strips are operative for holding said outside panels in said folded condition.

9. The adjustable sanitary napkin, panty liner or incontinence pad of claim 7 wherein at least a portion of said center adhesive strip remains exposed even with said end panels and said outside panels folded under said center panel for use in fastening said pad to an undergarment.

10. The adjustable sanitary napkin, panty liner or incontinence pad of claim 1 wherein at least a portion of said least one adhesive strip remains exposed even with all said end panels and either said inside panels or said outside panels folded under said center panel for use in fastening said pad to an undergarment.

11. The adjustable sanitary napkin, panty liner or incontinence pad of claim 1 wherein said end panels have a length of at least one quarter to one half a length of said center panel.

12. The adjustable sanitary napkin, panty liner or incontinence pad of claim 1 wherein said side panels have a width less than a width of said center panel.

13. The adjustable sanitary napkin, panty liner or incontinence pad of claim 12 wherein said inside panels have a width narrower than one half a width of said center panel.

14. The adjustable sanitary napkin, panty liner or incontinence pad of claim 1 wherein said center panel has a width of at least approximately 1.5 inches to 2.0 inches and a length of at least approximately 4.0 inches.

15. The adjustable sanitary napkin, panty liner or incontinence pad of claim 1 wherein said pad has a total pad length which is the sum of respective lengths of said two end panels and of said rectangular center panel.

16. An adjustable sanitary napkin, panty liner or incontinence pad of absorbent material having a pad edge, a top side and a bottom side;

a plurality of substantially straight line seams in said pad defining a center panel circumscribed by said pad edge thereby to define a plurality of end panels and side panels attached to said seams, said side panels each divided by an outside seam into an inside panel and an outside panel, such that one or more of said side panels may be folded or torn along said seams thereby to alter the shape and size of said pad, wherein said pad edge is diamond shaped with four pad edges and four pad corners and said center panel is rectangular having four panel corners each touching a respective one of said four pad edges at a location intermediate said pad corners thereby defining two said end panels and two said side panels each attached to one of said four seams.

17. The adjustable sanitary napkin, panty liner or incontinence pad of claim 16 wherein said pad edge is circular and said center panel is rectangular having four panel corners thereby to define two said end panels and two said side panels each attached to one of said four seams.

18. The adjustable sanitary napkin, panty liner or incontinence pad of claim 16 said seams having a seam thickness much smaller than a seam width between adjacent panels thereby to facilitate folding and tearing away of said panels along said seams.

19. An adjustable sanitary napkin, panty liner or incontinence pad of generally diamond shape with four pad edges and four pad corners, a top side and a bottom side;

four substantially straight seams in said pad defining a rectangular center panel having four panel corners each touching a respective one of said four pad edges at a location intermediate said pad corners thereby defining two end panels and two side panels each attached to one of said four seams such that said end panels and said side panels each taper to narrower ends, said side panels being each divided by an outside seam parallel into a inside panel and an outside panel;

such that one or more of said side panels may be folded or torn along said seams thereby to alter the shape and size of said pad; and a center adhesive strip on said bottom side for holding any of said end panels, said outside panels and said inside panels folded under said center panel for altering the shape and size of said pad;

an adhesive strip on said bottom side of each said inside panel and outside panel for holding either said outside panels folded under said inside panels and said center panel, or said inside panels folded under said center panel after tearing away each of said outside panels along said outside seam;

wherein said end panels have a length of at least one quarter to one half a length of said center panel, said side panels have a width less than a width of said center panel, said inside panels have a width narrower than one half a width of said center panel and said outside panels have outside ends which lie near each other and against said center adhesive strip when said outside panels are folded under said center panel; and wherein at least a portion of least one said adhesive strip remains exposed for use in fastening said pad to an undergarment even with all said end panels and either said inside panels or said outside panels folded under said center panel.

* * * * *